(12) United States Patent
Berg et al.

(10) Patent No.: US 6,960,233 B1
(45) Date of Patent: Nov. 1, 2005

(54) METHODS AND APPARATUS FOR IMPROVING THE FUNCTION OF BIOLOGICAL PASSAGES

(75) Inventors: Todd A. Berg, Stillwater, MN (US); Jeffrey G. Torborg, Rochester, MN (US)

(73) Assignee: Torax Medical, Inc., Maple Grove, MN (US)

( * ) Notice: Subject to any disclaimer, the term of this patent is extended or adjusted under 35 U.S.C. 154(b) by 0 days.

(21) Appl. No.: 10/732,696

(22) Filed: Dec. 9, 2003

Related U.S. Application Data

(60) Provisional application No. 60/432,684, filed on Dec. 10, 2002.

(51) Int. Cl.[7] .................................................. A61F 2/04
(52) U.S. Cl. .................................. 623/23.7; 623/23.64
(58) Field of Search ........................... 623/23.7, 23.64, 623/23.65, 23.68, 1.24–1.26; 606/153, 151, 606/139, 142, 196

(56) References Cited

U.S. PATENT DOCUMENTS

| | | | |
|---|---|---|---|
| 3,875,928 A * | 4/1975 | Angelchik .................... 600/37 |
| 4,271,827 A | 6/1981 | Angelchik .................. 128/1 R |
| 5,088,979 A * | 2/1992 | Filipi et al. .................... 604/26 |
| 5,234,447 A | 8/1993 | Kaster et al. ................ 606/153 |
| 5,234,448 A * | 8/1993 | Wholey et al. ............. 606/153 |
| 5,254,126 A * | 10/1993 | Filipi et al. ................. 606/146 |
| 5,387,235 A | 2/1995 | Chuter ........................... 623/1 |
| 5,403,326 A * | 4/1995 | Harrison et al. ............ 606/139 |
| 5,695,504 A | 12/1997 | Gifford, III et al. ........ 606/153 |
| 5,843,164 A | 12/1998 | Frantzen et al. ............... 623/1 |
| 5,876,448 A | 3/1999 | Thompson et al. ........... 623/12 |
| 5,887,594 A * | 3/1999 | LoCicero, III .............. 128/898 |
| 5,957,949 A | 9/1999 | Leonhardt et al. .......... 606/194 |
| 6,056,744 A * | 5/2000 | Edwards ....................... 606/41 |
| 6,073,052 A * | 6/2000 | Zelickson et al. .......... 607/100 |
| 6,136,006 A | 10/2000 | Johnson et al. ............. 606/108 |
| 6,146,416 A * | 11/2000 | Andersen et al. .......... 623/1.15 |
| 6,254,642 B1 * | 7/2001 | Taylor ...................... 623/23.64 |
| 6,302,917 B1 | 10/2001 | Dua et al. ................ 623/23.68 |

(Continued)

FOREIGN PATENT DOCUMENTS

WO     WO 00/059398     10/2000   .......... A61B 19/00

(Continued)

OTHER PUBLICATIONS

Sayre, J.T., Welch, J.P., "Current Experiences with the Management of Paraesophageal Hernias," Connecticut Medicine, vol. 44, No. 4, Apr. 1980, pp. 197-203.

(Continued)

*Primary Examiner*—Alvin Stewart
(74) *Attorney, Agent, or Firm*—Fish & Neave IP Group of Ropes & Gray LLP; Robert R. Jackson; Hong S. Lin

(57) ABSTRACT

Several methods and apparatus are available for treating patients that suffer from both gastro-esophageal reflux disorder and hiatal hernias. In order to treat these patients, an endoscopic probe may be used to push the herniated stomach below the diaphragm. In some embodiments, a two-part stent comprising a funnel stent and a reverse stent may be deployed to prevent a future re-herniation of the stomach and to reduce the annulus of the lower esophageal sphincter. In some embodiments, a reverse stent with perforating barbs may be deployed, in which the barbs penetrate the esophageal wall and attach to the diaphragm. In some embodiments, the crus muscles may be sutured together to reduce the hiatus size and a reverse stent may be deployed to reduce the annulus of the lower esophageal sphincter.

9 Claims, 9 Drawing Sheets

U.S. PATENT DOCUMENTS

| | | | |
|---|---|---|---|
| 6,409,723 B1 * | 6/2002 | Edwards | 606/41 |
| 6,432,040 B1 * | 8/2002 | Meah | 600/37 |
| 6,447,533 B1 * | 9/2002 | Adams | 606/213 |
| 6,547,776 B1 * | 4/2003 | Gaiser et al. | 604/506 |
| 6,551,328 B2 * | 4/2003 | Kortenbach | 606/139 |
| 6,592,596 B1 * | 7/2003 | Geitz | 606/139 |
| 6,663,639 B1 * | 12/2003 | Laufer et al. | 606/139 |
| 6,695,878 B2 * | 2/2004 | McGuckin et al. | 623/1.19 |
| 6,736,828 B1 * | 5/2004 | Adams et al. | 606/213 |
| 6,835,200 B2 * | 12/2004 | Laufer et al. | 606/153 |
| 2002/0078967 A1 * | 6/2002 | Sixto et al. | 128/898 |
| 2002/0082621 A1 * | 6/2002 | Schurr et al. | 606/151 |
| 2003/0018377 A1 * | 1/2003 | Berg et al. | 623/1.11 |
| 2003/0199987 A1 * | 10/2003 | Berg et al. | 623/23.64 |
| 2003/0220660 A1 * | 11/2003 | Kortenbach et al. | 606/151 |
| 2004/0044364 A1 * | 3/2004 | DeVries et al. | 606/213 |
| 2004/0254622 A1 * | 12/2004 | Shadduck | 607/99 |
| 2005/0085829 A1 * | 4/2005 | Kraemer et al. | 606/142 |
| 2005/0096750 A1 * | 5/2005 | Kagan et al. | 623/23.65 |

FOREIGN PATENT DOCUMENTS

| | | | |
|---|---|---|---|
| WO | WO 02/094132 | 11/2002 | A61F 2/00 |

OTHER PUBLICATIONS

Evanelisto, Mary, "How Do Some Smell Relief? S-u-r-g-e-r-y," Today's Surgical Nurse, vol. 19, No. 1, 1997, pp. 22-28.

Kahrilas, P.J. et al., "Hiatus Hernia," *The Esophagus,* Lippincott Williams & Wilkind, Castell, D.O. et al., Third Edition, 1999, pp. 381-396.

Branton, S.A. et al., "Surgical Treatment of Gastroesophageal Reflux Disease," *The Esophagus,* Lippincott Williams & Wilkins, Castell, D.O. et al., Third Edition, 1999, pp. 511-525.

"GI Endosopy: Therapies for GERD," Medtech Insight, Sep. 2001, pp. 236.

"Digestive Problems: Esophagus—GERD," MUSC Digestive Disease Center, www.ddc.musc.edu/ddc_pub/digestiveProbs/diseases/esophagus/GERD.htm.

"Patient Information: Laparoscopic Surgeries—Fundoplication," MUSC Digestive Disease Center, www.ddc.musc.edu/ddc_pub/patientInfo/surgeries/laparoscopic.fundoplication.htm.

* cited by examiner

METHODS AND APPARATUS FOR IMPROVING THE FUNCTION OF BIOLOGICAL PASSAGES

CROSS REFERENCE TO RELATED APPLICATION

This application claims the benefit of co-pending U.S. provisional patent application No. 60/432,684, filed Dec. 10, 2002, which is hereby incorporated by reference herein in its entirety.

BACKGROUND OF THE INVENTION

The present disclosure concerns apparatus and methods for improving the function of biological passages. The ability of biological passages to expand and contract actively or passively to regulate the flow of solids, liquids, gases, or combinations thereof, may be compromised by defects or disease. One example of a condition associated with decreased functionality of a body passage is Gastro Esophageal Reflux Disease (hereinafter, "GERD"), which affects the esophagus. Other body passages that may be subject to dysfunction, defect, and disease include, but are not limited to, a fallopian tube, a urethra (for example, in the case of incontinence), and a blood vessel (for example, in the case of an aneurysm). GERD and esophageal dysfunction will be further described herein for the sake of illustration.

The normal healthy esophagus is a muscular tube that carries food from the mouth through the chest cavity and into the upper part of the stomach. A small-valved opening in the distal esophagus, called the lower esophageal sphincter (hereinafter, "LES"), regulates the passage of food into the stomach. When functioning properly, the LES muscle presents a barrier to the reflux of acid or food back into the esophagus. The LES also regulates the stomach intra-gastric pressures, regulating acidic gases from refluxing from the stomach back into the esophagus. The LES, when functioning properly, will open to allow gases to be vented from the stomach. A healthy LES at rest can resist pressure from stomach gases that are at least 10 mm Hg greater than the normal intragastric pressure. This pressure difference can regulate the amount of acidic fluid that refluxes from the stomach into the esophagus. The LES is controlled largely by two components. The primary component is intrinsic smooth muscle of the distal esophagus wall. The second component is the skeletal muscle of the crural diaphragm or esophageal hiatus. The diaphragm is a muscle separating the stomach from the chest. Studies have shown that the diaphragm may act as a sphincter around the lower end of the esophagus. The esophageal hiatus is the opening in the diaphragm where the esophagus attaches to the stomach.

If the LES relaxes, atrophies, or degrades for any reason, the contents of the stomach, which may be acidic, are allowed back into the esophagus resulting in reflux symptoms. The major mechanism for esophageal reflux, which may be associated with GERD, is the relaxation of one or both of the LES or hiatal diaphragm sphincter mechanisms. Normally occurring mechanisms that diminish or prevent GERD include peristaltic squeezing by the esophageal body, gravity (when a person is in an upright position), and neutralization by saliva.

Chronic or excessive acid reflux exposure may cause esophageal damage. Drugs may be required to manage symptoms of the damage and medical intervention, including surgical or endoscopic procedures, may be required to repair the damage.

The lining of the esophagus is called mucosa. Chronic exposure to stomach gases may cause the mucosa to become inflamed or ulcerated. Inflamed or ulcerated mucosa may lead to problems that may require medical intervention.

Barrett's Esophagus is a disease of the esophagus that may compromise esophageal function. This disease may occur when the tissue that ordinarily lines the esophagus migrates away from the lower part of the esophagus to avoid exposure to the acidic fluids against the sensitive mucosa. Barrett's Esophagus is often a precursor to esophageal cancer.

The most common symptom of GERD is dyspepsia (commonly known as "heartburn"). Dyspepsia may be defined as an acute burning sensation in the chest area typically, behind the sternum. Other symptoms of GERD may include hemorrhage, pulmonary disorders, chronic cough, intermittent wheezing, ulcers, Barrett's Esophagus, and esophageal cancer.

A conventional treatment for GERD is surgical suturing of a pleat of tissue between the LES and stomach to make the lower esophagus tighter. Suturing may be performed endoscopically using a suturing device on the end of an endoscope inserted into the esophagus through the mouth. Endoscopic procedures are less invasive than open surgery, but still require surgical incisions and great skill.

Surgery, whether endoscopic or open may provide a basic mechanical correction. Surgical procedures may relocate and affix existing tissue of the stomach, esophagus, or both to add support and structure to the LES. LES strength is increased by the added support, thus reducing the incidence of reflux.

Another conventional treatment for GERD includes the use of pharmaceutical drugs. The drugs may include acid blockers that may reduce the production of acid by the stomach. The drugs may be effective to reduce the symptoms of mild GERD, but they do not treat LES dysfunction. In general, the drugs must be administered indefinitely to maintain their efficacy.

Hiatal hernias are often associated with GERD. A hiatal hernia is an anatomical abnormality in which part of the stomach protrudes through the diaphragm and up into the chest. This occurs when the diaphragm weakens and the inner lining of the abdomen pushes through the weakened area, forming a sac or hernia. If the esophageal hernia becomes enlarged (herniated), the LES function may be compromised and the risk of GERD increased.

The treatment methods described above only treat GERD, not hiatal hernias. One conventional surgical procedure for treating both GERD and hiatal hernias is fundoplication. In this procedure, the herniated portion of the stomach is pulled back into the stomach and the upper part of the stomach is wrapped around the lower part of the esophagus. This highly invasive procedure is often initially successful, but has a high risk of morbidity (including, e.g., infection and bleeding).

It is therefore an object of the present invention to develop treatments for GERD and hiatal hernias which are less invasive than fundoplication, yet are based on the principles of fundoplication.

SUMMARY OF THE INVENTION

These and other objects of the invention are accomplished in accordance with the principles of this invention by providing improved methods and apparatus for the treatment of GERD and hiatal hernias.

A common fundoplication procedure is the two-step Nissen fundoplication. The first step of the operation reduces the hiatal hernia in patients with a stomach herniation. This is accomplished by freeing the esophagus and the stomach of surrounding soft tissue connections around the hiatus and pulling the stomach and about 5 or 6 cm of the esophagus down into the abdomen. The muscles of the left and right crura are then approximated with typically two or three sutures placed behind the esophagus. This serves to tighten the hiatus back to a normal size so that the squeezing action generates a positive pressure, helping to block the reflux of stomach contents up into the esophagus.

The second step of the operation strengthens the function of the lower esophageal sphincter at the junction of the esophagus and the stomach. This is achieved by freeing the fundus of the stomach of its connections, for example, the short gastric vessels to the spleen and the ligaments to the left diaphragm. Once freed, a window is made behind the esophagus. This window allows the surgeon to pull the redundant portion of the fundus of the stomach from the left side behind the esophagus to the right side, and then around the front of the esophagus to be sewn to itself, typically with three stitches. The three stitches usually span a distance of about 2 cm. If the span is longer, the patient can experience difficulties with swallowing after the operation.

It would be desirable to strengthen the function of the lower esophageal sphincter at the junction of the esophagus and the stomach without the wrapping of the stomach. By avoiding wrapping the stomach, some of the consequences such as dysphasia, torsion of the esophagus, and an inclusion of the gastric corpus in the wrap may also be avoided.

One potential treatment method for GERD and hiatal hernias is internal fundoplication and this method is based on the dynamics of a Nissen fundoplication, but is non-invasive and does not require wrapping of the stomach. The procedure is comprised of a two-step process and includes the use of an endoscopic probe and a two part stent with one segment utilizing reverse stent technology and a second segment comprising an expandable funnel stent.

In the first step of the procedure, a standard endoscopic probe may be used to push the herniated stomach below the diaphragm and position the gastro-esophageal junction to be consistent with the diaphragm.

The second step involves inserting a catheter directly into the esophagus through the mouth to the desired location below the gastro-esophageal junction. A protective sheath may be removed to deploy the funnel stent inside the stomach. Next, the reverse stent may be positioned immediately below the lower esophageal sphincter for deployment. An illustrative reverse stent that may be used in the internal fundoplication method is described in Berg et al. U.S. patent application Ser. No. 10/134,306, filed Apr. 26, 2002, which is hereby incorporated by reference in its entirety.

The funnel stent may be expandable and may attach to the stomach wall to secure the complete stent. The primary purpose of the funnel stent is to eliminate the possibility of the stomach migrating through the diaphragm and re-herniating. Furthermore, the funnel stent reduces the possibility of the reverse stent segment migrating upward into the esophagus.

The diaphragmatic suturing method is another possible treatment for patients with GERD and a hiatal hernia. This method is a two-step process that utilizes an endoscopic probe and the deployment of a reverse stent with perforating barbs. First, a standard endoscopic probe may be used to push the herniated stomach below the diaphragm and to position the gastroesophageal junction to be consistent with the diaphragm.

The reverse stent may be positioned and deployed immediately below the lower esophageal sphincter. The barbs on the stent may perforate the esophageal wall and attach to the hiatal diaphragm tissue. Perforating the esophagus and attaching the device to the diaphragm eliminates the chance of the stomach migrating above the diaphragm, while tightening the crus muscles. An illustrative reverse stent that may be used in the diaphragmatic suturing method is described in Berg et al. U.S. patent application Ser. No. 10/134,306, filed Apr. 26, 2002, which is hereby incorporated by reference in its entirety.

The reverse stent and laparoscopic suturing method is another procedure that may be used to treat patients with GERD and a hiatal hernia. The first step of this approach is to use an endoscopic probe to reposition the herniated stomach below the diaphragm. This approach combines the endoscopic deployment of the reverse stent and the suturing of the right and left crus muscles via a laparoscopic procedure. The primary purpose of the reverse stent is to fix the mechanics of the lower esophageal sphincter. An illustrative reverse stent that may be used in the reverse stent and laparoscopic suturing method is described in Berg et al. U.S. patent application Ser. No. 10/134,306, filed Apr. 26, 2002, which is hereby incorporated by reference in its entirety. The primary purpose of the laparoscopic suturing of the crus muscles is to tighten the diaphragm, thus reducing the chance the stomach re-herniates through the hiatus, and to bolster continence of the gastroesophageal junction.

Further features of the invention, its nature and various advantages will be more apparent from the accompanying drawings and the following detailed description of the preferred embodiments.

DETAILED DESCRIPTION OF THE PREFERRED EMBODIMENTS

Although hiatal hernias and GERD are not necessarily interrelated, many patients who suffer from GERD also suffer from hiatal hernias. Hiatal hernias can be categorized into three main categories.

Figure 1A:
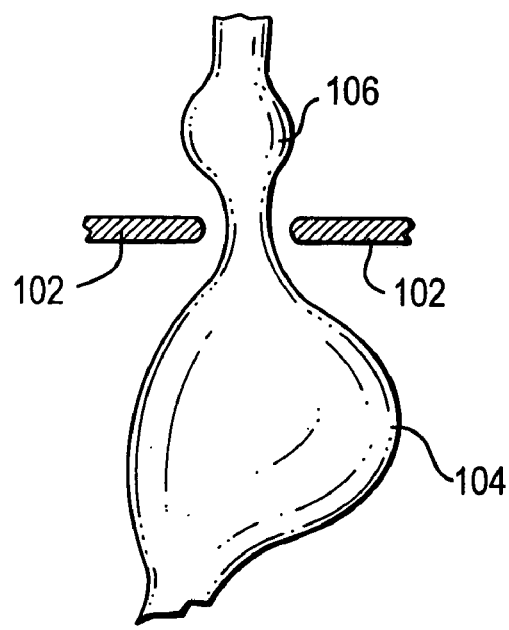
FIGS. 1A–1C show three different types of hiatal hernias.
Figure 1B:
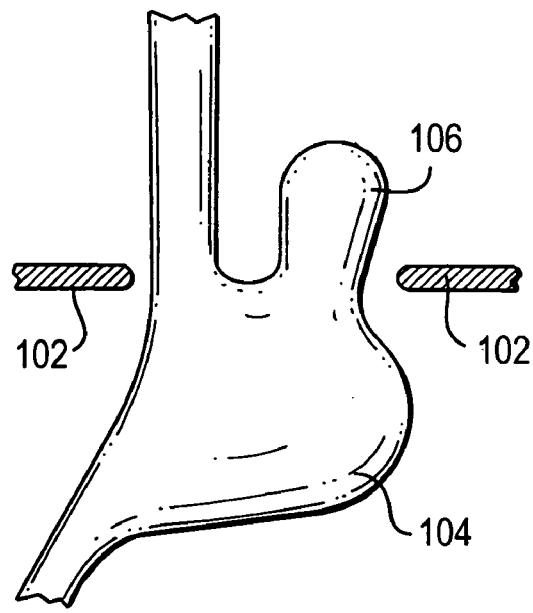
Figure 1C:
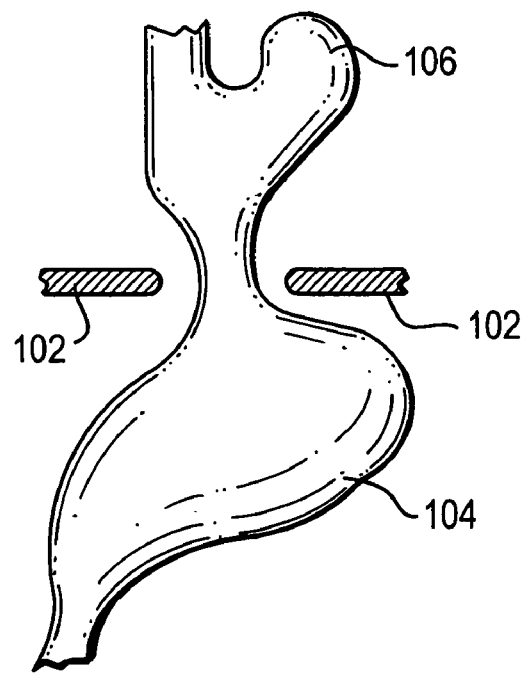

FIGS. 1A–1C show three types of hiatal hernias. An illustrative sliding hiatal hernia is shown in FIG. 1A. Generally, a diaphragm 102 separates a stomach 104 from the esophagus. In a sliding hiatal hernia, the gastro-esophageal junction between the esophagus and stomach 104, that is normally at or below the diaphragm, migrates above the diaphragm into the esophagus. Sliding hiatal hernias are most commonly associated with GERD, however the sliding hiatal hernia is frequently asymptomatic. Sliding hiatal hernias are more likely to occur than other forms of hiatal hernias.

An illustrative true paraesophageal hiatal hernia is shown in FIG. 1B. In a true paraesophageal hiatal hernia, the gastro-esophageal junction remains below diaphragm 102, however, a portion of the stomach 106 migrates above diaphragm 102.

An illustrative mixed paraesophageal hiatal hernia is shown in FIG. 1C. The mixed paraesophageal hiatal hernia has characteristics of both the sliding hiatal hernia and the true paraesophageal hiatal hernia. As shown in FIG. 1C, both stomach 106 and the gastro-esophageal junction migrate above diaphragm 102.

Patients may develop paraesophageal hiatal hernias shown in FIGS. 1B and 1C from sliding hiatal hernias. The paraesophageal hiatal hernia may be associated with more serious symptoms such as bleeding or gastric volvulus. Other symptoms may include pain (which often follows meals and occurs in the upper abdomen or substernal region), vomiting (occurring in less than half of the cases), anemia, and significant heartburn (occurring in about a third of the cases). There are no effective non-operative management options for these patients; the presence of a paraesophageal hernia is an indication for surgical repair in most instances.

The association of hiatal hernias with GERD is furthered by the effect hiatal hernias may have on GERD severity. In some cases, hiatal hernias may trap the acidic stomach contents in the hernial sac, thus making the stomach contents more available to reflux during LES relaxation. In some cases, the hiatal hernia may also contribute to esophageal injury. The likelihood to develop reflux disease may increase with increasing hernia size. The sliding hiatal hernia, for instance, impacts reflux both by affecting the competence of the gastro-esophageal junction in preventing reflux and in compromising the process of esophageal acid clearance once reflux occurs.

Figure 2A:
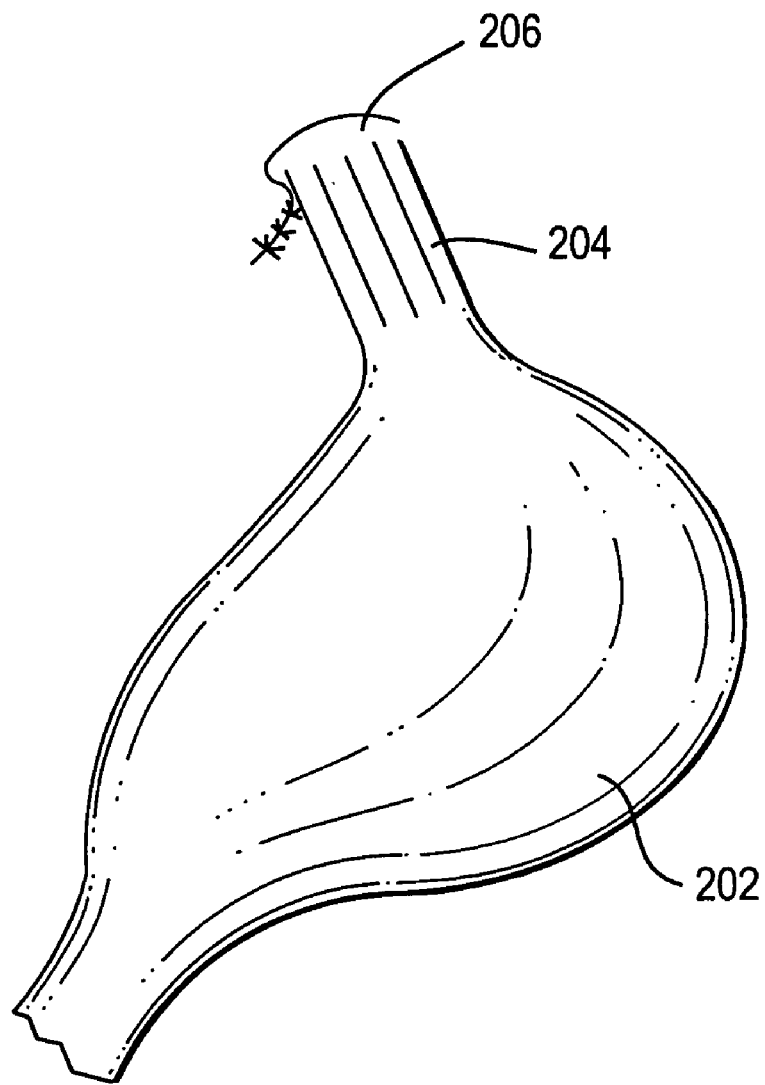
FIGS. 2A–2C show a fundoplication being performed on a herniated stomach.
Figure 2B:
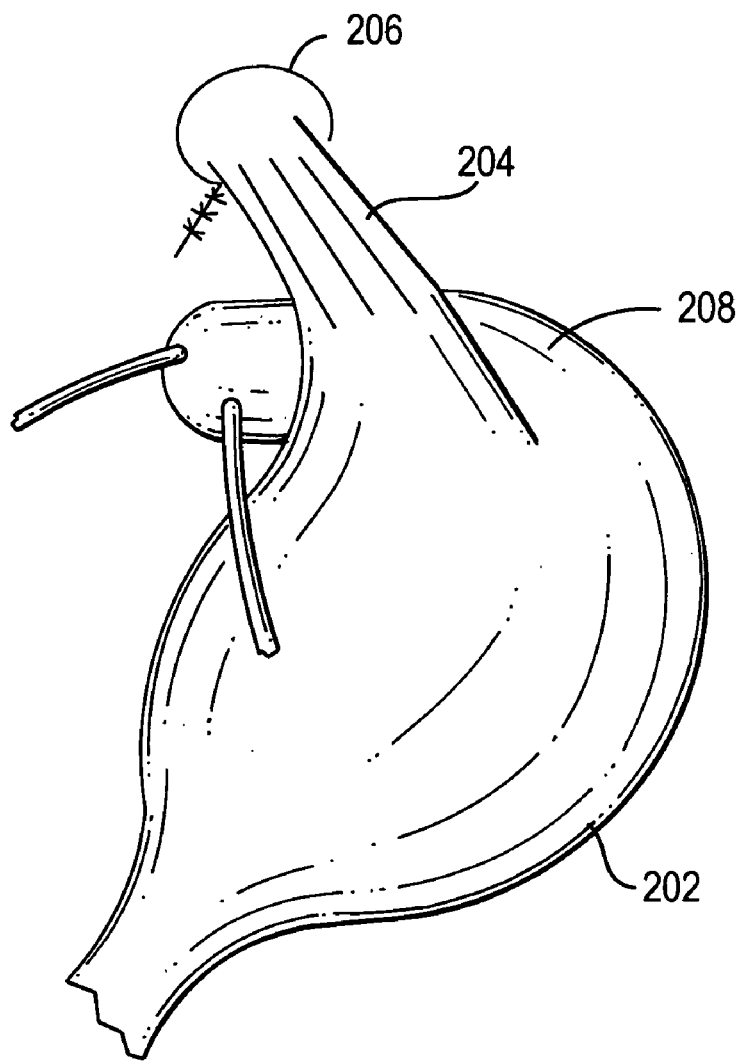
Figure 2C:
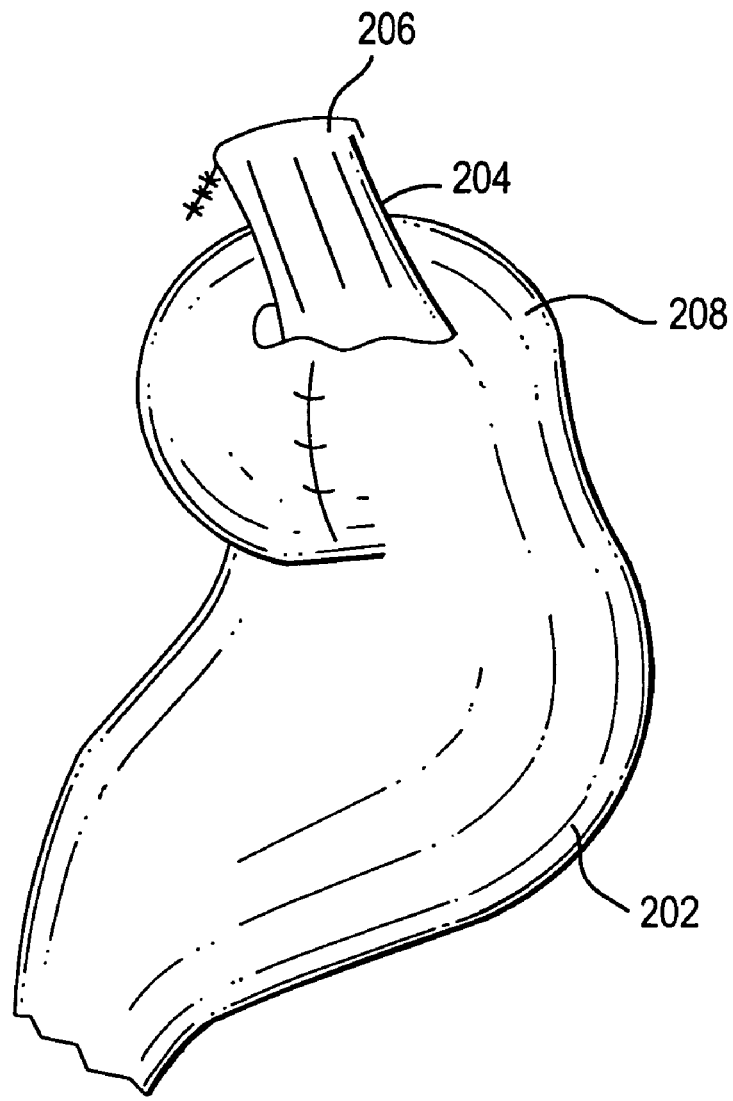

A Nissen fundoplication may be performed on a patient suffering from both GERD and a hiatal hernia, shown in FIGS. 2A–2C. The Nissen fundoplication is completed in a two-step process. The first step reduces the hiatal hernia in patients with a stomach herniation. The second step strengthens the function of the lower esophageal sphincter at the junction of the esophagus and the stomach.

FIG. 2A shows stomach 202 and esophagus 204 after the first step of the Nissen fundoplication has been performed. The first step is accomplished by first separating esophagus 204 and stomach 202 of surrounding soft tissue connections around hiatus 206 (i.e. the opening in the diaphragm). Next, the herniated portion of stomach 202 and a portion of esophagus 204 are pulled through hiatus 206 and into the abdomen. In some embodiments, only 5–6 cm of the esophagus is pulled into the abdomen. The size of hiatus 206 may be reduced to prevent future herniation of the stomach. To accomplish this, the left and right crura surrounding hiatus 206 may be sewn together with, for example, two or three sutures placed behind the area where esophagus 204 passes through hiatus 206. These sutures approximate the left and right crura of the diaphragm by tightening hiatus 206 back to a normal size so that the squeezing action generates a positive pressure, helping to block the reflux of stomach contents up into esophagus 204.

The second step of the Nissen fundoplication is shown in FIGS. 2B and 2C. This step strengthens the LES at the junction of the esophagus and the stomach. First, a fundus 208 (the portion of the stomach that lies above the cardiac notch) is freed of all connections, such as, for example, the short gastric vessels to the spleen and the ligaments to the diaphragm. As shown in FIG. 2B, once fundus 208 is freed, a window is made behind esophagus 204 around which fundus 208 may be pulled. Fundus 208 may be pulled around to the front of the esophagus. In some embodiments, fundus 208 may be pulled to the side of the esophagus.

As shown in FIG. 2C, fundus 208 may be sutured onto itself with, for example, two or three stitches. It may be desirable to limit the span of the stitches to 2 cm to allow the patient to swallow normally after the procedure.

The Nissen fundoplication may be performed laparoscopically, which involves creating several small incisions in which to insert the tools necessary to perform the procedure. Although this procedure is less invasive than open surgery, the patient may suffer from bleeding and infections at the site of surgery after receiving a fundoplication. The present invention introduces the uses of stents in addition to other endoscopic procedures to provide improved methods and apparatus for treating GERD and hiatal hernias. In particular, the methods and apparatus will focus on treatment of sliding and mixed paraesophageal types of hiatal hernias.

A suitable method for the treatment of GERD and sliding or mixed paraesophageal hiatal hernias is the internal fundoplication method. This procedure is based on the principles of the Nissen fundoplication method, however, instead of being performed laparoscopically or laparotomically, the procedure is performed endoscopically. In an endoscopic procedure, no incisions are made, instead existing body passages provide access to the site of treatment. The first step of this procedure is shown in FIGS. 3A and 3B, in which the herniated stomach is pushed below the diaphragm.

Figure 3A:
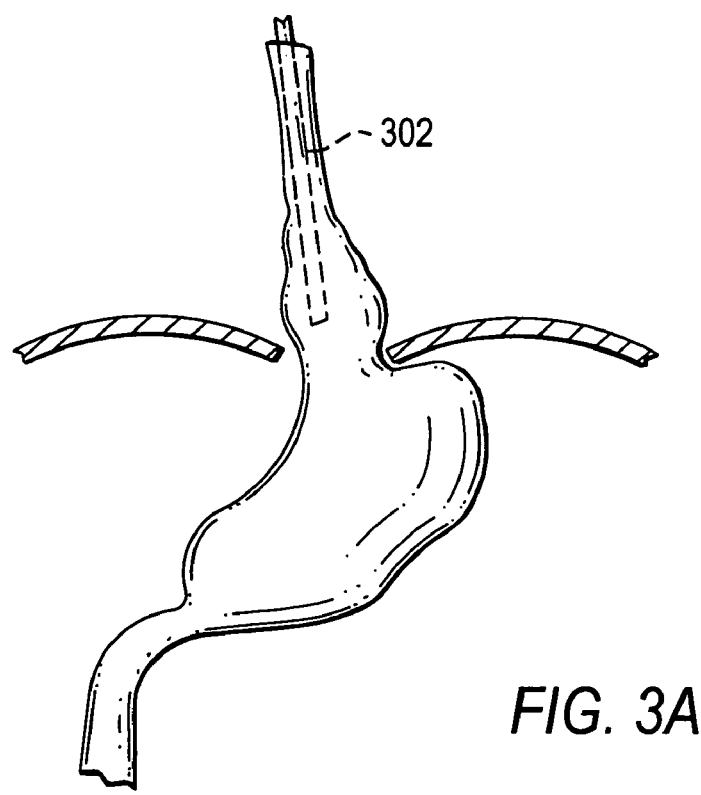
FIGS. 3A and 3B show an illustrative endoscopic process for repositioning a hiatal hernia under the diaphragm in accordance with some embodiments of the present invention.
Figure 3B:
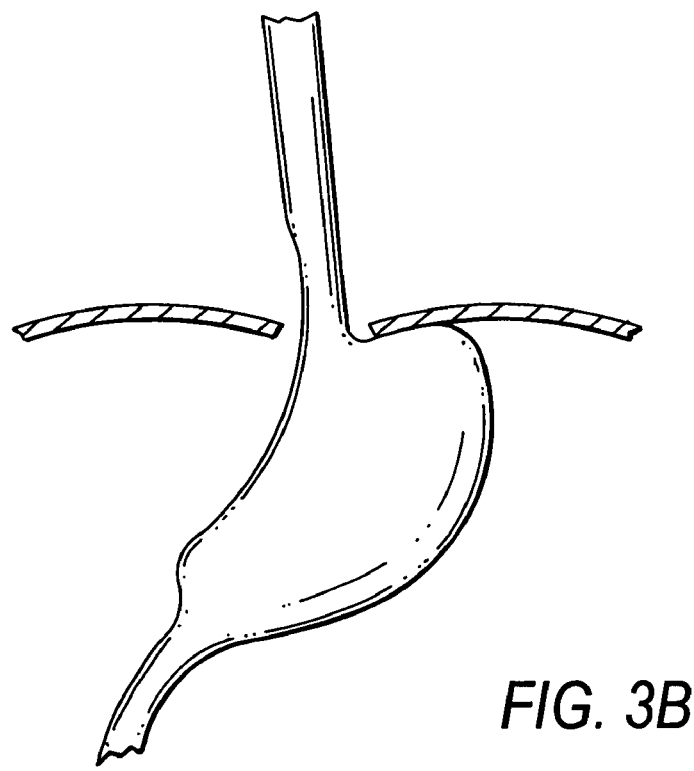

FIGS. 3A and 3B show the illustrative use of an endoscopic probe 302 to reposition the gastro-esophageal junction in accordance with some embodiments of the present invention. Preferably, endoscopic probe 302 may be inserted into the esophagus through the patient's mouth. When the tip of endoscopic probe 302 reaches the portion of the stomach that has herniated through the hiatus, probe 302 may be used to push the stomach through the hiatus and into the abdomen. When the hernia has been repositioned and the gastroesophageal junction is no longer in the esophagus, then endoscopic probe 302 may be removed. As shown in FIG. 3B, the stomach has been repositioned with endoscopic probe 302.

The second step of the internal fundoplication method involves deploying a two-part stent within the esophagus and stomach. The two-part stent comprises a funnel stent 350 and a reverse stent 360.

Figure 3C:
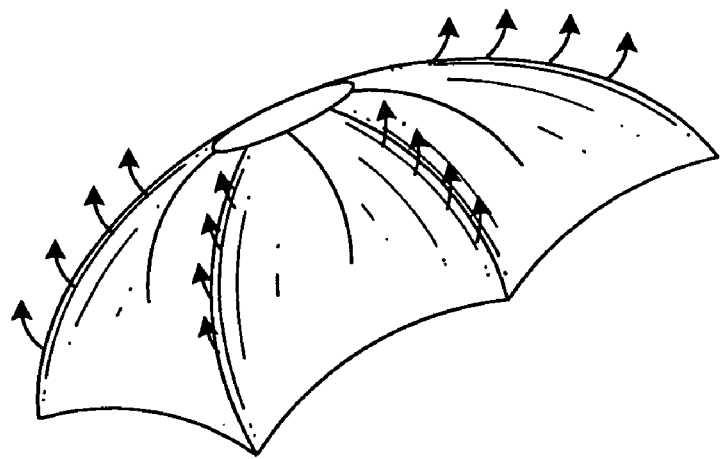
FIG. 3C shows an illustrative funnel stent that may be used to prevent the stomach from migrating through the diaphragm in accordance with some embodiments of the present invention.

FIG. 3C shows an illustrative funnel stent 350 in accordance with some embodiments of the present invention. Funnel stent 350 may be deployed at the upper portion of a stomach to prevent the stomach from migrating into the esophagus and reherniating. A catheter may be used to insert an initially compressed funnel stent 350 into the stomach. After funnel stent 350 is pushed out of the catheter into the stomach, funnel stent 350 may expand. The barbs on the exterior of funnel stent 350 may pierce and hold the stomach tissue, keeping funnel stent 350 fixed.

Figure 3D:
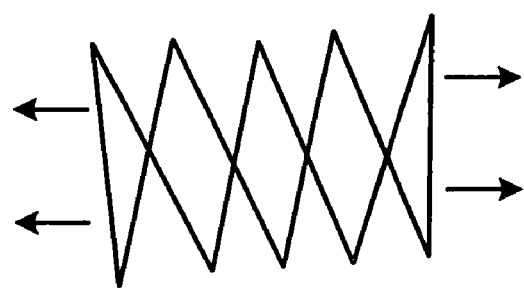
FIG. 3D shows an illustrative reverse stent that may correct defects in the lower esophageal sphincter in accordance with some embodiments of the present invention.

FIG. 3D shows an illustrative reverse stent 360 in accordance with some embodiments of the present invention. Reverse stent 360 may be deployed immediately below the lower esophageal sphincter to tighten the sphincter and reduce the amount of stomach contents that may reflux into the esophagus. Reverse stent 360, unlike funnel stent 350, exerts an inward force. In some embodiments, reverse stent 360 may be delivered using the same catheter as funnel stent 350 by inserting reverse stent 360 behind funnel stent 350 in the catheter. In some embodiments, the catheter may be removed after deploying funnel stent 350 to load reverse stent 360 into the catheter. Reverse stent 360 may contain barbed fingers on the exterior to engage the esophageal tissue and to draw the tissue inward. In some embodiments, a balloon may be utilized to expand reverse stent 360 to engage the barbs to the esophageal wall.

Figure 3E:
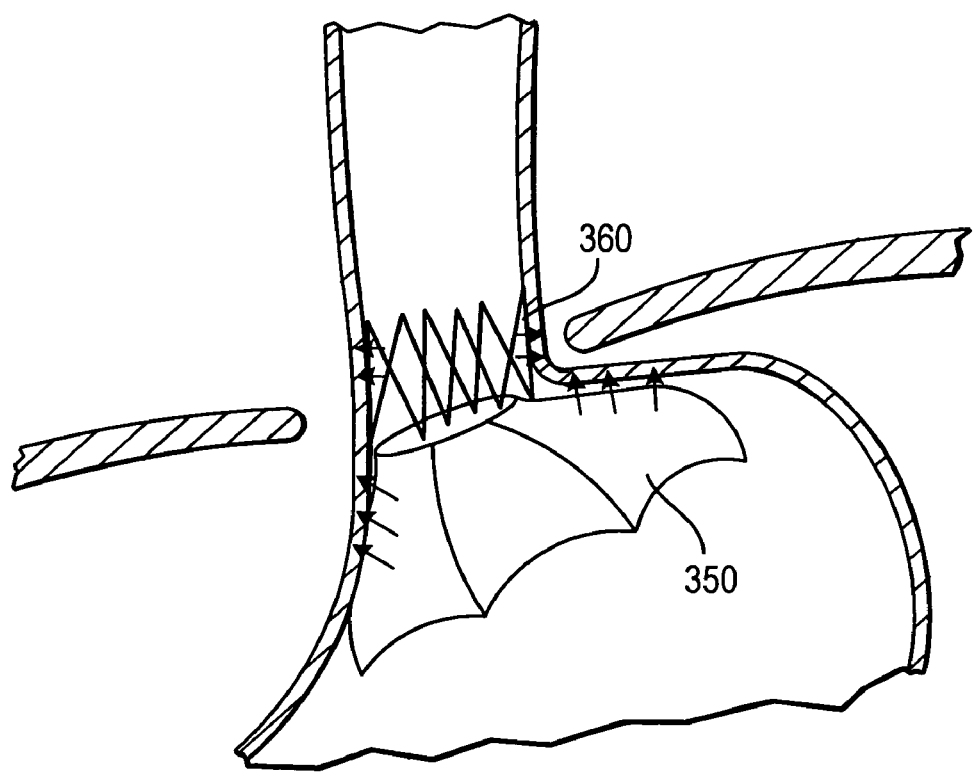
FIG. 3E shows an illustrative funnel stent and an illustrative reverse stent deployed in accordance with some embodiments of the present invention.

FIG. 3E shows a completed internal fundoplication procedure in accordance with some embodiments of the present invention. As shown in FIG. 3E, funnel stent 350 is fully expanded at the top of the stomach to prevent the stomach from migrating through the hiatus. As shown in FIG. 3E, reverse stent 360 is deployed below the lower esophageal sphincter and acts to pull the esophageal wall inward to reduce the annulus of the LES and prevent reflux of stomach contents into the esophagus.

Another procedure that may treat GERD and sliding or mixed paraesophageal types of hiatal hernias is the diaphragmatic suturing method. The diaphragmatic suturing method is a two-step method that involves repositioning the hiatal hernia and deploying a reverse stent with perforating barbs.

The first step of the diaphragmatic suturing method is shown in FIGS. 3A and 3B, which involves using endoscopic probe 302 to reposition the gastro-esophageal junction and to push the herniated portion of the stomach back into the stomach.

Figure 4A:
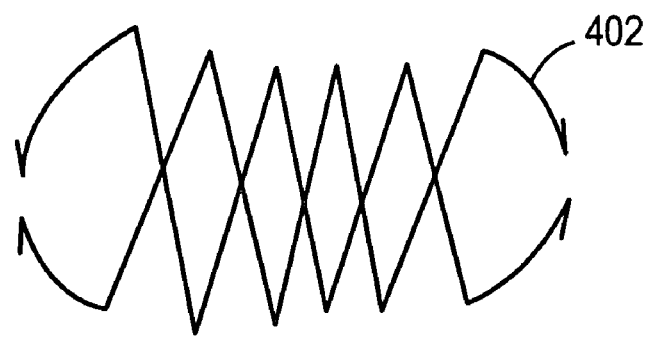
FIG. 4A shows an illustrative reverse stent with extended barbs that attach to the diaphragm in accordance with some embodiments of the present invention.

The second step of the diaphragmatic suturing method involves deploying a reverse stent with perforating barbs at the lower esophageal sphincter. FIG. 4A shows a reverse stent 402 with perforating barbs in accordance with some embodiments of the present invention. Reverse stent 402 includes long barbs that are intended to penetrate the esophageal wall and attach to the diaphragm. When the barbs are attached to the diaphragm, the inward force of reverse stent 402 pulls together the diaphragm, tightens the crus muscles, and decreases the size of the hiatus. In addition, inward force exerted by reverse stent 402 reduces the annulus size of the lower esophageal sphincter.

Figure 4B:
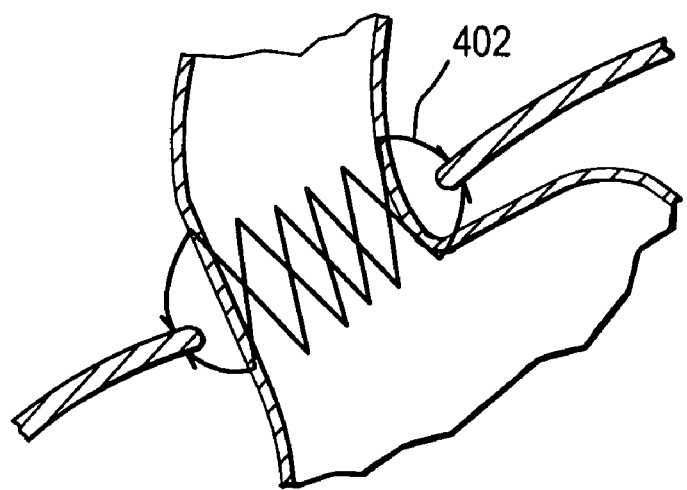
FIG. 4B shows an illustrative reverse stent attached to the esophagus and diaphragm in accordance with some embodiments of the present invention.

FIG. 4B shows reverse stent 402 attached to the esophagus and diaphragm in accordance with some embodiments of the present invention. The gastro-esophageal junction should be prevented from migrating above the diaphragm because the barbs hold both the diaphragm and the esophagus.

Another procedure for treating GERD and sliding or mixed paraesophageal types of hiatal hernias is the reverse stent and laparoscopic suturing method.

This method is a two-step method. The first step of the laparoscopic suturing method involves repositioning the hiatal hernia as described above, and shown in FIGS. 3A and 3B. Next, the left and right crus muscles of the diaphragm are sutured together laparoscopically to reduce the size of the hiatus and tighten the diaphragm. This step reduces the chance of the stomach re-herniating through the hiatus and bolsters the continence of the gastro-esophageal junction.

The second step involves deploying a reverse stent, similar to reverse stent 360 shown in FIG. 3D. As stated earlier, reverse stent 360 may be delivered from a catheter and expanded to engage its barbs to the esophageal tissue using a balloon.

Figure 5:
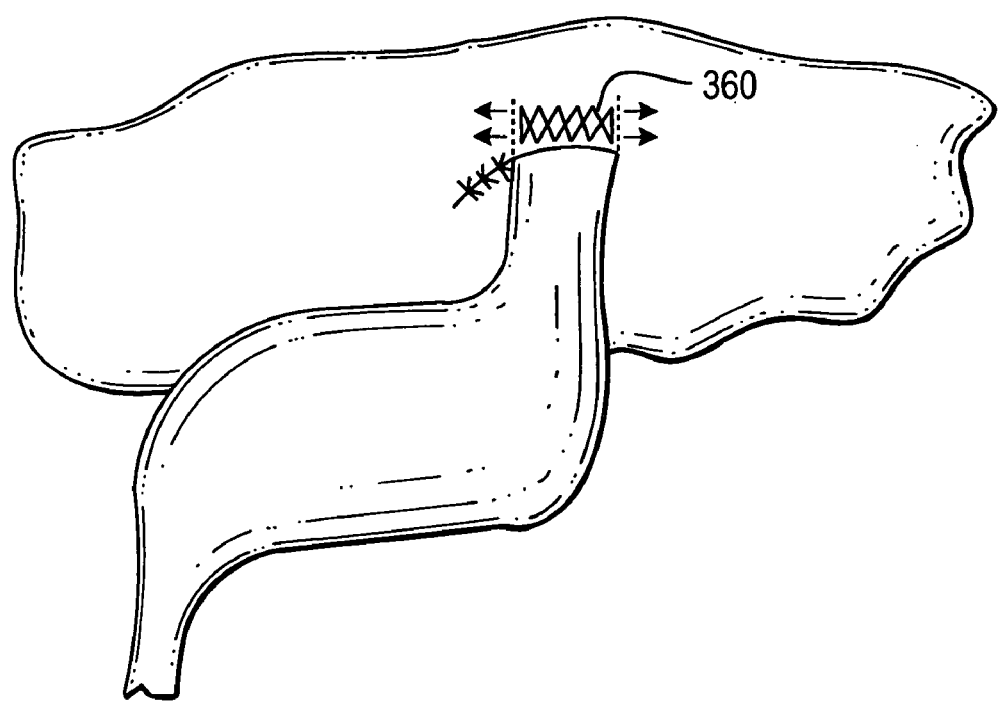
FIG. 5 shows an illustrative result of a reverse stent and laparoscopic suturing procedure that has been performed in accordance with some embodiments of the present invention.

FIG. 5 shows an illustrative gastro-esophageal system after the reverse stent and laparoscopic suturing procedure has been performed in accordance with some embodiments of the present invention.

The foregoing is merely illustrative of the principles of this invention and various modifications can be made by those skilled in the art without departing from the scope and spirit of the invention.

What is claimed is:

1. A method for treating a patient with a hiatal hernia and gastro-esophageal reflux disorder, the method comprising:
   pushing the patient's herniated stomach below the patient's diaphragm using an endoscopic probe;
   inserting a first catheter through the patient's mouth to the patient's stomach, wherein the first catheter contains a compressed funnel stent;
   releasing the funnel stent, wherein the funnel stent expands and engages to the patient's stomach and prevents the stomach from re-herniating through the patients diaphragm;
   inserting a second catheter through the patient's mouth to the patient's lower esophageal sphincter, wherein the second catheter contains a reverse stent;
   releasing the reverse stent from the second catheter;
   expanding the reverse stent to engage the patient's esophageal tissue; and
   releasing the reverse stent, such that the reverse stent draws the patient's esophageal tissue inwards to decrease the annulus of the lower esophageal sphincter.

2. The method of claim 1, wherein the funnel stent includes barbs arranged on its exterior.

3. The method of claim 1, wherein the reverse stent includes barbs arranged on its exterior.

4. The method of claim 1, wherein the reverse stent is expanded using a balloon.

5. A method for treating a patient with a hiatal hernia and gastro-esophageal reflux disorder, the method comprising:
   pushing the patient's herniated stomach below the patient's diaphragm using an endoscopic probe;
   inserting a catheter through the patient's mouth to the patient's stomach, wherein the catheter contains a reverse stent with perforating barbs;
   releasing the reverse stent from the catheter;
   expanding the reverse stent, wherein the barbs engage the patient's esophageal tissue and diaphragm; and
   releasing the reverse stent, such that the reverse stent draws the patient's esophageal tissue and diaphragm inwards to strengthen the patient's crus muscles and decrease the annulus of the patient's lower esophageal sphincter.

6. The method of claim 5, wherein the reverse stent is expanded using a balloon.

7. A method for treating a patient with a hiatal hernia and gastro-esophageal reflux disorder, the method comprising:

pushing the patient's herniated stomach below the patient's diaphragm using an endoscopic probe;

suturing the patient's left and right crus muscles laparoscopically to reduce the size of the hiatus;

inserting a catheter through the patient's mouth to the patient's lower esophageal sphincter, wherein the catheter contains a reverse stent;

releasing the reverse stent from the catheter;

expanding the reverse stent to engage the patient's esophageal tissue; and releasing the reverse stent, wherein the reverse stent draws the patient's esophageal tissue inwards to decrease the annulus of the patient's lower esophageal sphincter.

8. The method of claim 7, wherein the reverse stent contains barbs arranged on its exterior.

9. The method of claim 7, wherein the reverse stent is expanded using a balloon.

* * * * *